(12) United States Patent
Paspa et al.

(10) Patent No.: US 6,606,521 B2
(45) Date of Patent: Aug. 12, 2003

(54) IMPLANTABLE MEDICAL LEAD (75) Inventors: Paul M. Paspa, Los Gatos, CA (US); C. Lance Boling, San Jose, CA (US)

(73) Assignee: Neuropace, Inc., Mountain View, CA (US)

( * ) Notice: Subject to any disclaimer, the term of this patent is extended or adjusted under 35 U.S.C. 154(b) by 0 days.

(21) Appl. No.: 09/901,854

(22) Filed: Jul. 9, 2001

(65) Prior Publication Data

US 2003/0009207 A1 Jan. 9, 2003

(51) Int. Cl.$^7$ ................................................ A61N 1/05
(52) U.S. Cl. ........................................................ 607/116
(58) Field of Search ................................. 607/115, 116, 607/45, 134, 135, 136, 137, 138; 600/378, 373, 377, 544

(56) References Cited

U.S. PATENT DOCUMENTS

| | | |
|---|---|---|
| 3,850,161 A | 11/1974 | Liss |
| 4,541,440 A * | 9/1985 | Parsonnet |
| 4,596,559 A | 6/1986 | Fleischhacker |
| 4,735,208 A | 4/1988 | Wyler et al. |
| 4,850,359 A | 7/1989 | Putz |
| 4,869,255 A | 9/1989 | Putz |
| 4,903,702 A | 2/1990 | Putz |
| 4,979,511 A | 12/1990 | Terry, Jr. |
| 5,031,618 A | 7/1991 | Mullett |
| 5,097,835 A | 3/1992 | Putz |
| 5,116,345 A | 5/1992 | Jewell et al. |
| 5,129,903 A | 7/1992 | Luhr et al. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,251,634 A | 10/1993 | Weinberg |
| 5,255,691 A | 10/1993 | Otten |
| 5,351,394 A | 10/1994 | Weinberg |
| 5,464,446 A | 11/1995 | Dreessen et al. |
| 5,531,778 A | 7/1996 | Maschino et al. |
| 5,540,730 A | 7/1996 | Terry, Jr. et al. |
| 5,560,358 A | 10/1996 | Arnold et al. |
| 5,571,150 A | 11/1996 | Wernicke et al. |
| 5,603,703 A | 2/1997 | Elsberry et al. |
| 5,676,655 A | 10/1997 | Howard, III et al. |
| 5,683,422 A | 11/1997 | Rise |
| 5,702,429 A | 12/1997 | King |
| 5,707,396 A | 1/1998 | Benabid |
| 5,707,400 A | 1/1998 | Terry, Jr. et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,752,979 A | 5/1998 | Benabid |
| 5,782,798 A | 7/1998 | Rise |
| 5,792,186 A | 8/1998 | Rise |
| 5,792,217 A | 8/1998 | Camps et al. |
| 5,797,945 A | 8/1998 | Saifi |
| 5,800,459 A | 9/1998 | Spano et al. |
| 5,800,474 A | 9/1998 | Benabid et al. |
| 5,814,092 A | 9/1998 | King |
| 5,817,106 A | 10/1998 | Real |
| 5,843,093 A | 12/1998 | Howard, III |

(List continued on next page.)

FOREIGN PATENT DOCUMENTS

EP 0 347 658 B1 12/1989

*Primary Examiner*—Scott M. Getzow
(74) *Attorney, Agent, or Firm*—Morrison & Foerster LLP (57) ABSTRACT

The present invention generally provides an implantable medical lead having markings. The lead is easier to implant and improves the accurate localization of lead electrodes at a specific point of the brain for neurostimulation. Also provided is an implantable medical lead having a removable extension that advantageously provides a minimal length of excess lead protruding from the lead insertion site. The improved lead and method of implantation facilitates use of a neurostimulator device that is implanted directly in a patient's cranium.

34 Claims, 7 Drawing Sheets

U.S. PATENT DOCUMENTS

| | | |
|---|---|---|
| 5,843,148 A | 12/1998 | Gijsbers et al. |
| 5,843,150 A | 12/1998 | Dreessen et al. |
| 5,902,236 A | 5/1999 | Iversen |
| 5,913,882 A | 6/1999 | King |
| 5,938,689 A | 8/1999 | Fischell et al. |
| 5,948,007 A | 9/1999 | Starkebaum et al. |
| 5,978,702 A | 11/1999 | Ward et al. |
| 6,006,124 A | 12/1999 | Fischell et al. |
| 6,011,996 A | 1/2000 | Gielen et al. |
| 6,016,449 A | 1/2000 | Fischell et al. |
| 6,018,094 A | 1/2000 | Fox |
| 6,018,682 A | 1/2000 | Rise |
| 6,024,702 A | 2/2000 | Iversen |
| 6,038,481 A | 3/2000 | Werner et al. |
| 6,094,598 A | 7/2000 | Elsberry et al. |
| 6,109,269 A | 8/2000 | Rise et al. |
| 6,109,270 A | 8/2000 | Mah et al. |
| 6,142,994 A | 11/2000 | Swanson et al. |
| 6,162,101 A | 12/2000 | Fischer et al. |
| 6,163,729 A | 12/2000 | Kuzma |
| 6,179,826 B1 | 1/2001 | Aebischer et al. |
| 6,188,932 B1 | 2/2001 | Lindegren |
| 6,192,279 B1 * | 2/2001 | Barreras et al. |
| 6,210,346 B1 | 4/2001 | Hall et al. |
| 6,210,417 B1 | 4/2001 | Baudino et al. |

\* cited by examiner

IMPLANTABLE MEDICAL LEAD

TECHNICAL FIELD

The present invention relates to implantable medical leads, and more particularly, to leads designed for improved lead positioning and placement.

BACKGROUND

In medical diagnosis and treatment of various brain disorders, including epilepsy, Parkinson's disease, sleep disorders, and psychiatric ailments, it is customary and frequently useful to analyze electrical signals originating in the brain. It is also becoming accepted to apply electrical stimulation to various structures of the brain for both diagnostic and therapeutic purposes. Furthermore, chronic electrical stimulation is contemplated as a direct treatment for various disorders. For example, an implantable neurostimulator that is coupled to an implantable medical lead having one or more deep brain electrodes or depth electrodes is described in U.S. Pat. No. 6,016,449 to Fischell, et al.

Generally, external equipment, such as a cranially implantable neurostimulator device, is connected to acutely implanted brain electrodes located on an implantable medical lead. Typical implantable medical leads are flexible small-diameter (usually 1–1.5 mm) round leads having one or more distal electrodes located coaxially along the distal end of the lead. It is also possible to employ an implantable medical lead having scalp electrodes instead of depth electrodes for certain types of electroencephalogram monitoring and analysis along the scalp; however, precise localization of the electrode is less feasible with scalp electrodes.

Generally, implantation of an implantable medical lead involves surgically exposing an insertion site in the cranium that is an operative distance from an electrode site. An electrode site may be chosen at any appropriate stage of the surgical procedure, including pre-surgically in an operative planning stage; intraoperatively after a craniotomy has been performed or a burr hole has been made; or intraoperatively after one or more other procedures, such as functional mapping, have been performed. After an insertion site is created, the lead is then inserted to the desired electrode site along a predetermined direction to a predetermined depth.

Common requirements for implantable medical leads include flexibility, strength, and durability. The extent of such qualities, of course, is dependent upon the nature of the use, for example, temporary or permanent implantation. While material selection and certain construction techniques can be tailored to assist in meeting these prescribed characteristics, one consideration in the design of implantable leads is increasing the ease with which the delicate lead is implanted.

Figure 1A:
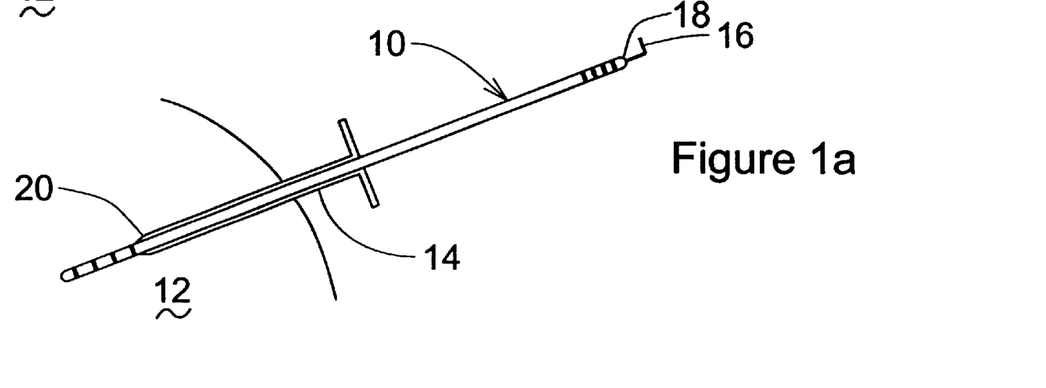
FIGS. 1a–1d illustrate a conventional lead placement technique.

A conventional lead placement technique is illustrated in FIGS. 1a–1d. Referring first to FIG. 1a, a traditional deep brain lead 10 is shown positioned in a desired deep brain structure 12 with the assistance of a cannula 14, a rigid tunneling and positioning tool capable of sliding over the brain lead 10. Positioning the lead 10 is complicated by the fact that existing leads do not provide a visual indicator showing how deep the lead 10 has been inserted and/or whether the lead 10 has been accidentally moved. Even one millimeter of travel of a properly positioned lead may cause unsatisfactory results. Accordingly, reliable methods and apparatus for locating the lead in the brain are necessary.

Figures 1B, 1C:
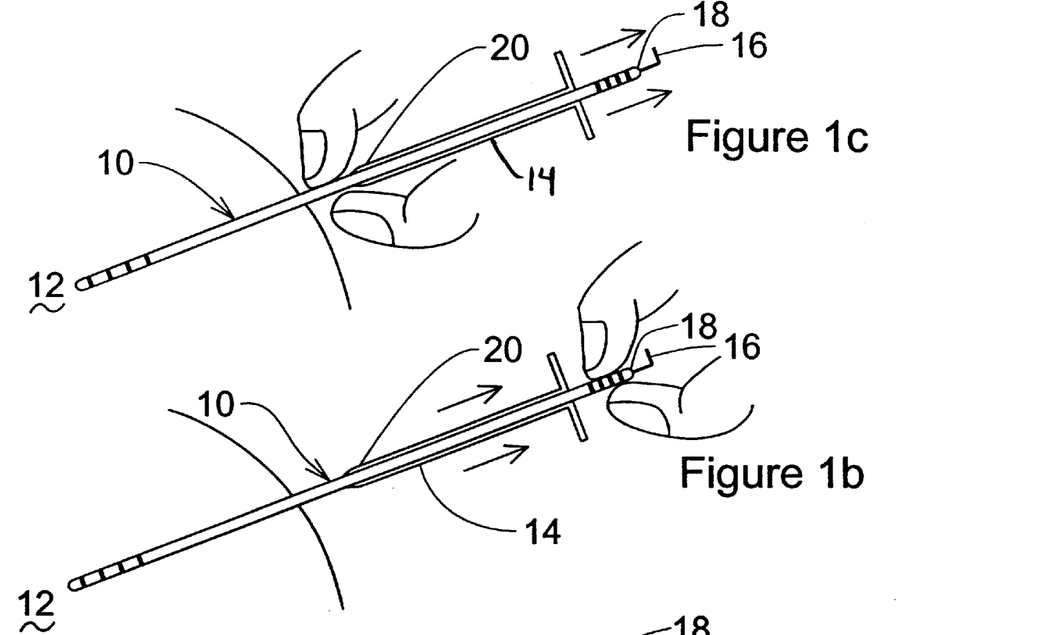

Referring now to FIG. 1b, after the cannula 14 and lead 10 is appropriately placed, the cannula 14 is retracted. While the cannula 14 is retracted, a stylet 16 inserted at a proximal end 18 of the lead 10 may be employed to hold the lead 10 in place. The lead 10 and its position within the brain must be continually monitored to ensure proper placement.

After the cannula 14 is retracted such that its distal end 20 is exposed as shown in FIGS. 1b and 1c, the physician grasps the exposed portion of the lead 10 adjacent to the distal end 20 of the cannula 14, holds it in position, and releases the stylet 16 so that the cannula 14 can be removed by sliding it longitudinally over the lead 10. If a split cannula is employed, it may be removed in a lateral direction without sliding the cannula longitudinally over the lead 10. However, removal of a split cannula in a lateral direction may risk damage to the delicate lead 10 as well as risk dislocation of the lead 10.

Figure 1D:
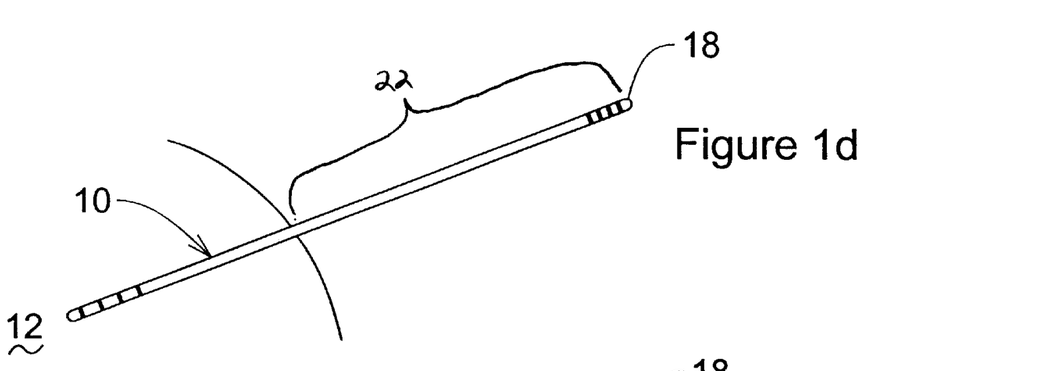

Finally, the stylet 16 must be removed without grossly affecting the position of the lead 10. A positioned lead 10 with the stylet 16 removed is shown in FIG. 1d. As can be seen in FIGS. 1a–1d, the length 22 of the lead 10 remaining outside the insertion site is approximately at least as long as the cannula 14 itself so that the lead 10 may be held in position during installation. However, the length 22 of the lead 10 that remains outside the brain may be too long for aesthetic reasons as well as for functional attachment to a cranially implanted neurostimulator device. Also, a long lead segment 22 outside the cranium may create a site for traction on the lead 10 potentially resulting in its dislocation and/or a site for potential damage to the lead 10 itself. In some circumstances, leads with an excess of coiled-up length may have an increased susceptibility to reliability problems.

In general, implanting a lead within the brain is difficult and, therefore, a lead that is easy to implant is desirable. A lead that is easier to implant improves the accurate localization of the electrode at a specific point of the brain. As a result, subsequent treatment can be carried out more precisely. Also desirable is a lead that advantageously has a minimal length of excess lead protruding from the insertion site.

SUMMARY OF THE INVENTION

In accordance with one aspect of the present invention, there is provided an implantable lead including a body having a proximal end and a distal end. At least one electrode is located at the distal end and connected to at least one terminal that is located at the proximal end. The lead includes a plurality of markings on the body.

In accordance with another aspect of the present invention, there is provided a method of implanting a lead. The method includes providing a lead that has a proximal end and a distal end. The lead has at least one electrode at the distal end that is connected to at least one terminal at the proximal end. The lead includes a plurality of markings located between the distal end and the proximal end. The method includes the step of determining an electrode site for stimulation. An insertion site is provided in the patient's cranium and the lead is inserted into the insertion site. The lead is positioned and a visual indication of lead position is provided by the markings on the lead.

In accordance with yet another aspect of the present invention, there is provided an implantable lead comprising a lead portion having a proximal end and a distal end. The lead portion further includes a body between the proximal end and the distal end. The lead portion also includes at least one electrode at the distal end and at least one terminal at the proximal end. The at least one electrode is connected to the at least one terminal. The implantable lead further includes an extension removably connected to the lead portion. The extension has a proximal end and a distal end. The extension includes a body between the proximal end and the distal end.

In accordance with another aspect of the present invention, there is provided an implantable lead comprising a lead portion having a proximal end and a distal end. The lead portion further includes at least one electrode at the distal end electrically connected to at least one terminal at the proximal end. The implantable lead further includes an extension removably connected to the lead portion at a breakaway zone. The extension has a proximal end and a distal end.

In accordance with another aspect of the invention there is provided an implantable lead. The implantable lead includes a lead portion having a proximal end and a distal end. The lead portion includes at least one electrode at the distal end and at least one terminal at the proximal end. The at least one electrode is electrically connected to the at least one terminal. The implantable lead further includes an extension removably coupled to the lead portion. The extension has a proximal end and a distal end. The extension includes a sleeve portion that has a fixed end and a lead portion receiving end. The fixed end is fixed to the distal end of the extension. The lead portion is removably coupled within the lead portion receiving end of the sleeve.

In accordance with yet another aspect of the present invention, there is provided a method of implanting a lead in a patient's brain comprising the step of providing a lead that has a lead portion and an extension. The lead portion is removably coupled to the extension. The lead portion has at least one electrode at a distal end that is electrically coupled to at least one terminal at the proximal end. The method further includes determining an electrode site for stimulation. An insertion site is provided in the patient's cranium and a cannula is inserted into the patient's brain. The lead is inserted into the cannula such that the distal end of the lead portion is inserted first. The lead is positioned at the electrode site and the cannula removed. The extension is removed from the lead portion.

BRIEF DESCRIPTION OF THE DRAWINGS

The foregoing and other advantages of the invention will become apparent upon reading the following detailed description and upon reference to the drawings in which.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DETAILED DESCRIPTION

Figure 2:
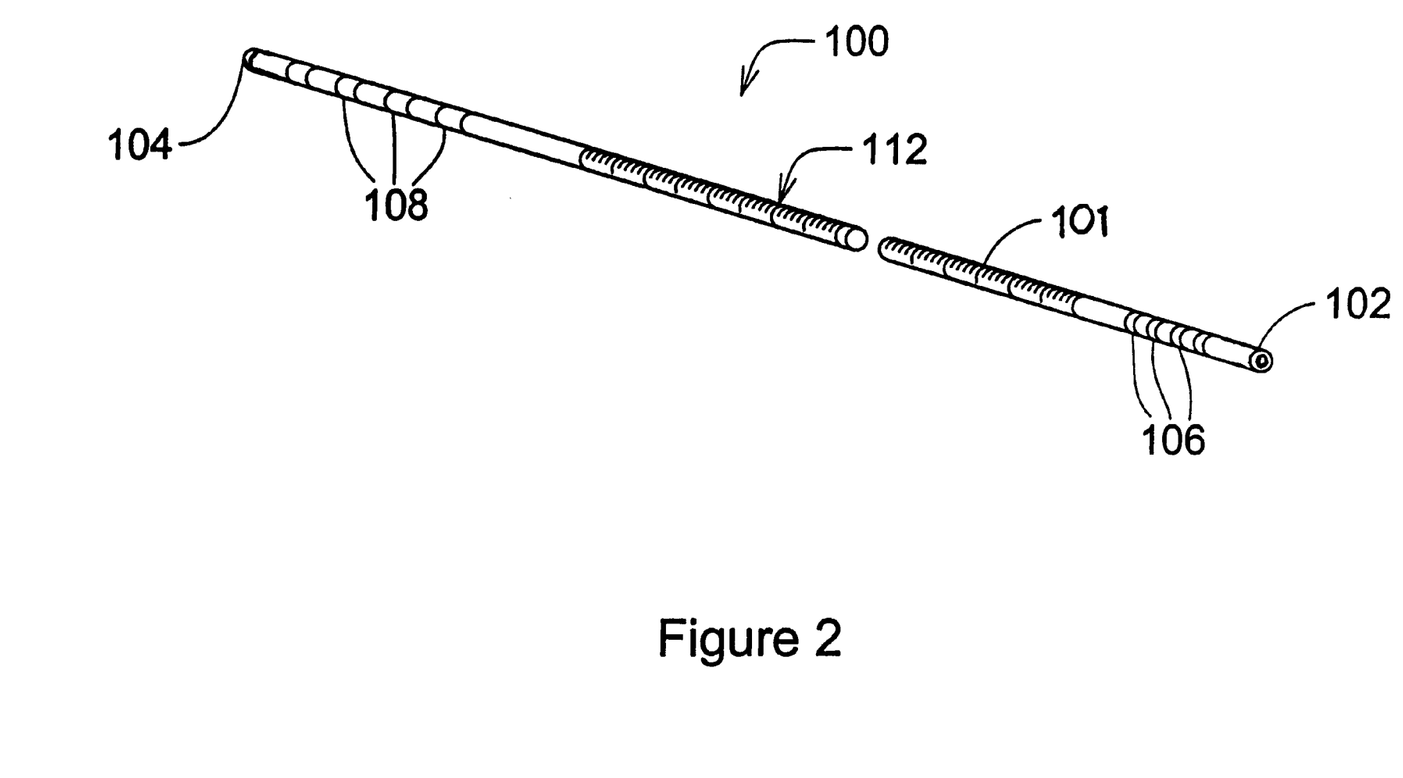
FIG. 2 is a lead of the present invention.

Referring initially to FIG. 2, an implantable medical lead 100 is illustrated. For the purposes of this specification and claims, the term "lead" is used herein in its broadest sense and includes a stimulation lead, a sensing lead, a combination thereof or any other elongated member, such as a catheter, which may usefully be passed through an insertion site such as a cranial burr hole.

The lead 100 includes a proximal end 102 and a distal end 104 and a body 101 extending therebetween. The proximal end 102 includes a plurality of electrically conductive terminals 106 for operatively coupling the proximal end 102 to a neurostimulator device or some kind of equipment. The distal end 104 includes at least one electrically conductive electrode 108 to electrically stimulate or for sensing the patient's brain. While typically each terminal 106 is electrically connected to a single electrode 108 by a conductor (shown in FIG. 3), a terminal 106 can be connected to two or more electrodes 108. Terminals 106, electrodes 108 and conductors are preferably formed of a non-corrosive, highly conductive material such as stainless steel, platinum, or platinum alloys such as a platinum-iridium alloy.

It should further be noted that sensors other than electrodes 108 may be employed. For example, a temperature sensor (e.g., a thermocouple), a chemical concentration sensor (such as a dissolved oxygen sensor), or a pressure sensor may be advantageously employed in lieu of one or more of the distal electrodes 108 in some variations.

The body 101 is made primarily from a medical grade, substantially inert material such as silicone, urethane or any of a number of suitable biocompatible materials. The body 101 provides a flexible and durable exterior structure for the components of the lead 100 and insulate adjacent terminals 106 and/or electrodes 108. Serving as a sheath, the body 101 contains the internalized elements of the lead 100. For example, the body 101 provides an enclosure for each conductor that connects a terminal 106 with one or more electrodes 108.

The body 101 further includes a plurality of markings 112, preferably graduated markings 112 located along the outside of the body 101, preferably between the electrodes 108 and terminals 106. The markings 112 provide the physician with a visual indication of the depth to which the lead 100 has been inserted during the implant procedure and/or whether the lead 100 has been accidentally moved. Various markings 112 are within the scope of the invention. For example, any markings such as markings 112 indicating length in metric or English units, with or without numerals or letters are within the scope of the invention. Also, the markings 112 need not be graduated and nor be equally spaced, as long as the markings 112 are useful to the physician in locating the lead 100 during implantation. Even if the lead 100 stretches while being positioned, the markings 112 provide a gross estimate of positioning indication that is useful to the physician.

The markings 112 are generally formed by using a silicone-based adhesive with carbon black pigment that is transferred to the body 101. This technique is employed for radio-opaque or non-radio-opaque embodiments. In one variation, the markings 112 are printed on the body 101 of the lead 100 using ion beam assisted deposition. Various materials including metallic or ceramic materials are used for the markings 112 to provide biocompatibility or radio-pacity. Alternative methods known in the art may be used for creating the markings 112. In one variation, the markings 112 are made of radio-opaque material to facilitate implantation when X-ray or other known techniques are used during the installation. Non-radio-opaque markings 112 are also within the scope of the invention.

The body 101 of the lead 100 has a diameter between approximately 0.5 mm and approximately 2.0 mm, preferably has a diameter between 1.0 and 1.3 mm. In general, a smaller diameter is better, consistent with sufficient ruggedness and ease of handling for surgical applications. A suitable overall length for the lead 100 is between approximately 250 and 500 mm.

Figure 3:
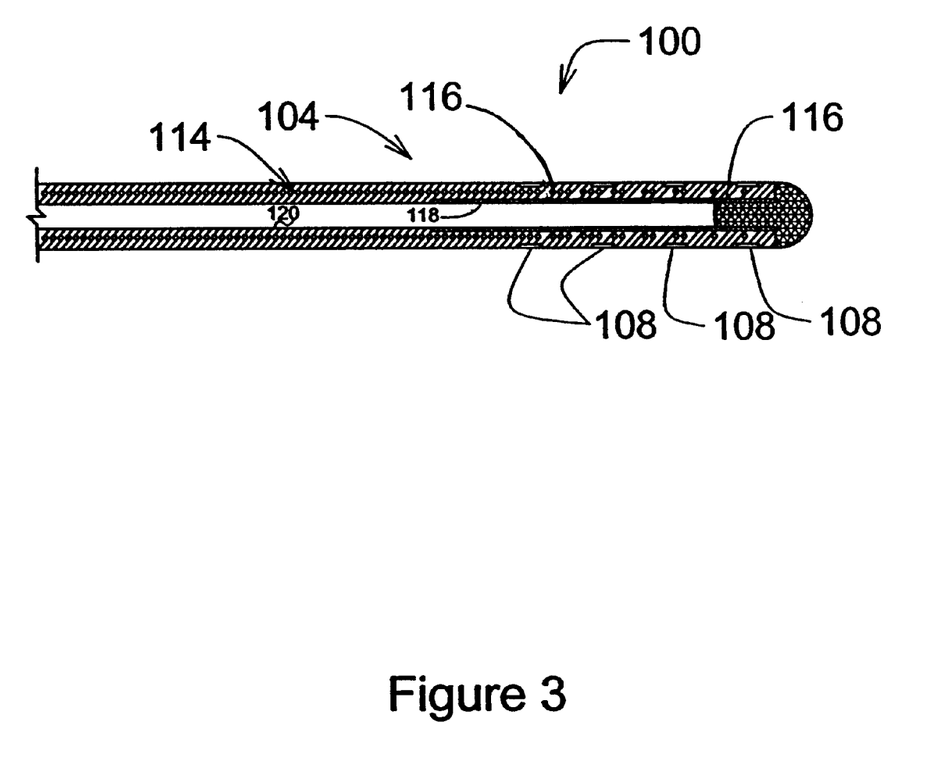
FIG. 3 is a cross-sectional view of a lead of the present invention.

FIG. 3 illustrates an exemplary longitudinal cross section of a lead 100 representative of a distal end 104. The lead 100 of FIG. 3 includes four ring electrodes 108 on a single distal end 104. Varying the number of electrodes 108 may vary the illustrated structure in ways that should be apparent. It should be noted that the cross-section of FIG. 3 may also be representative of a proximal end 102; the construction is preferably similar or identical, though dimensions and some materials may vary.

The distal end 104 of the lead 100 illustrated in FIG. 3 includes a helically arranged conductor set 114 that includes four independently insulated conductors 116, one for each of the electrodes 108. Each of the conductors 116 in the conductor set 114 is affixed to and in conductive communication with a respective one of the electrodes 108.

Although the conductor set 114 is depicted in FIG. 3 as helical, or coiled about the longitudinal axis of the distal end to provide some longitudinal resilience, the conductors 116 may alternatively extend longitudinally through the distal end 104, particularly in the case of a single uninsulated conductor. Each conductor 116 is formed of a conductive material such as stainless steel, platinum, or platinum-iridium alloy. The conductor set 114 exhibits the desired mechanical properties of low resistance, corrosion, resistance, flexibility, and strength.

The electrodes 108 are fabricated as rings arranged around and somewhat embedded into the flexible body 101. A portion of the distal end 104 includes a reinforcing tube 118, preferably fabricated from a more rigid polymer material such as polyimide, polyamide, or polyetheretherketone (PEEK). Together the body 101 and the tube 118 define a longitudinal lumen 120, which maybe employed to receive a stylet to facilitate implantation. A stylet may not always be necessary, especially if the distal end 104 is sufficiently rigid from the use of a helical conductor set 114 and/or reinforcing tube 118.

The tip of the distal end 104 is closed by a relatively rigid plug 122 adapted to fit within the reinforcing tube 118, or if no such tube 118 is present, within the body 101. The plug 122 is preferably fabricated from a relatively rigid biocompatible polymer, and is crimped, glued, molded, or fused in place. It should be observed that numerous materials are possible for the plug 122, body 101, and reinforcing tube 118. Various categories of polymers and plastics such as polyester, polyimide, polyamide, polyetheretherketone (PEEK), and specific materials falling into those categories such as nylon and aramid (e.g., Kevlar®), are particularly well suited.

Figure 4A:
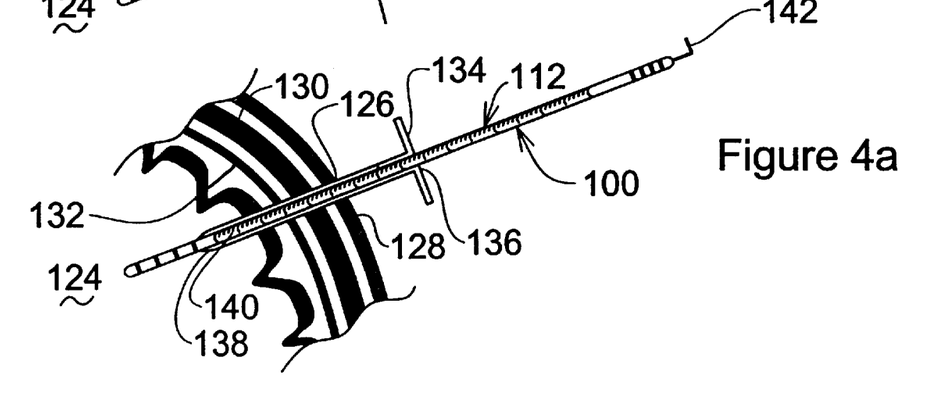
FIGS. 4a–4d illustrate a lead placement technique of the present invention.

Placement of a graduated depth lead 100 is now discussed in reference to FIGS. 4a–4d. An electrode site 124 is chosen at any appropriate stage of the surgical procedure, including pre-surgically in an operative planning stage; intraoperatively after a craniotomy has been performed or a burr hole 126 has been made; or intraoperatively after one or more other procedures, such as functional mapping, have been performed. Referring first to FIG. 4a, after an incision in the patient's scalp 128 is formed, an insertion site or bore hole 126 is formed in the patient's cranium 130. An incision is made in the dura mater 132 and a cannula 134 is inserted.

The cannula 134 may be of any commercially available type. Generally, it has an open proximal end 136, an open distal end 138, and a central bore 140. Prior to insertion, the cannula 134 may be provided with an obturator (not shown) to assist in penetrating the tissue structure. The obturator is inserted into the central bore 140 of the cannula 134 to close the central bore 140 of the cannula 134 and prevent tissue from entering the cannula 134 during insertion. The cannula 134 is generally constructed of surgical stainless steel or other material.

Still referencing FIG. 4a, with the cannula 134 in position and the obturator removed, a brain lead 100 is passed into the bore 140 of the cannula 134 until positioned in a desired deep brain structure. The positioning of the brain lead 100 is assisted with a stylet 142. The stylet 142, or guide wire is designed to be inserted into the lumen 120 of the brain lead 100 to assist in positioning the brain lead 100. The brain lead 100 is gently pushed into the cannula 134 to the electrode site 124. The positioned brain lead 100 is shown in FIG. 4a. Alternate methods and devices may be used to achieve similar results.

As seen in FIG. 4a, the markings 112 on the body 101 of the brain lead 100 provide the physician with a visual indicator of how much of the brain lead 100 has been inserted. The markings 112 appearing outside of the cannula 134 are viewed. Also, markings 112 that are not outside of the cannula 134 are viewed using X-ray, fluoroscopy, and other known techniques during the installation. Viewing the markings 112 at any location along the brain lead 100 and at any stage of the implantation procedure facilitates accurate placement and positioning of the brain lead 100. Also, with the brain lead 100 in position, the markings 112 serve as indicator in the event the brain lead 100 is accidentally moved during the remainder of the procedure and after the procedure is completed.

Figures 4B, 4C, 4D:
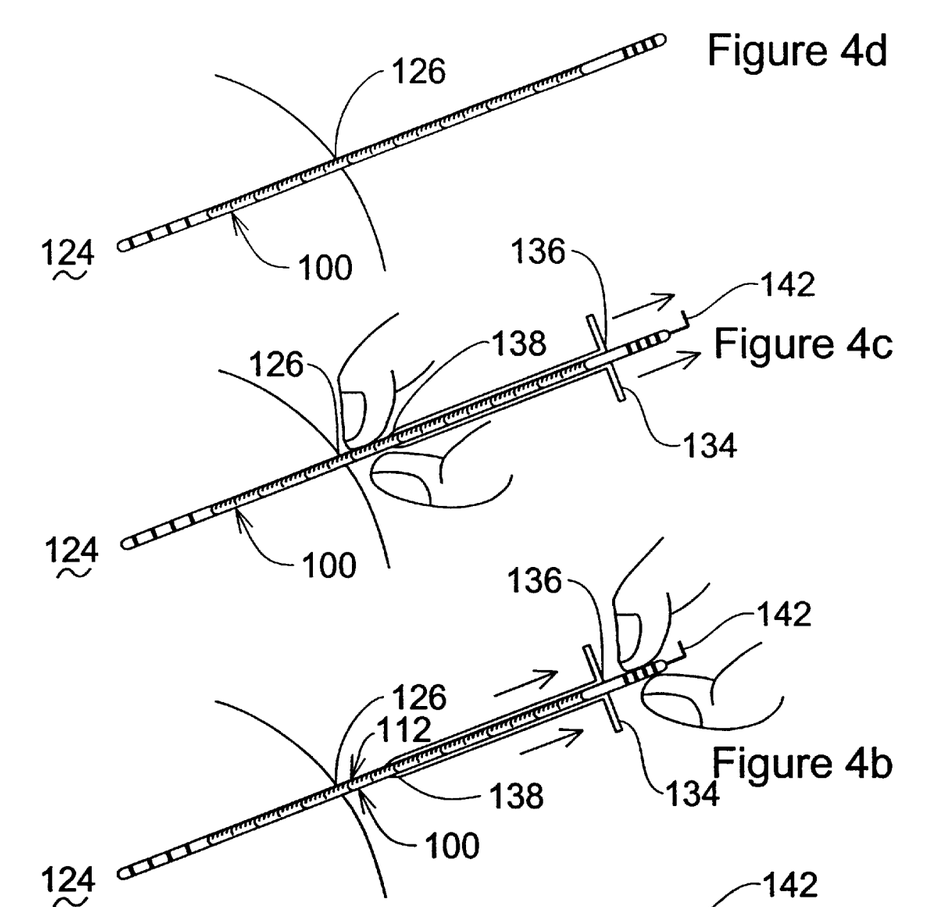

Referring now to FIG. 4b, after the cannula 134 and lead 100 is appropriately placed, the cannula 134 is retracted. As the cannula 134 is retracted, a stylet 142 may be employed to hold the lead 100 in place. The lead 100 and its position within the brain must be continually monitored to ensure proper placement.

After the cannula 134 is retracted such that its distal end 138 is exposed at the insertion site as shown in FIGS. 4b and 4c, the physician releases the stylet 142 and grasps the exposed portion of the brain lead 100 adjacent to the distal end 138 of the cannula 134. The physician holds the brain lead 100 in position so that the cannula 134 can be removed by sliding it longitudinally over the brain lead 100. If a split cannula is employed, it may be removed in a lateral direction without sliding the cannula longitudinally over the lead. However, removal of a split cannula in a lateral direction may risk damage to the delicate lead 100 as well as risk dislocation of the lead 100. In either case, the markings 112 on the brain lead 100 assist in keeping the brain lead 100 stationary by providing a visual indication of whether the brain lead 100 has been moved while the cannula 134 is being extracted.

Finally, the stylet 142 must be removed without grossly affecting the positioning of the lead 100. A positioned lead 100 with the stylet 142 removed is shown in FIG. 4d. Again, the markings 112 on the brain lead 100 assist in maintaining the lead 100 in position as the stylet 142 is removed from the lumen 120 of the brain lead 100. Also, fine positioning of lead 100 either before or after removal of the stylet 142 is aided by the markings 112 as they are viewed outside the cranium 130 or within the cranium 130.

Figure 5:
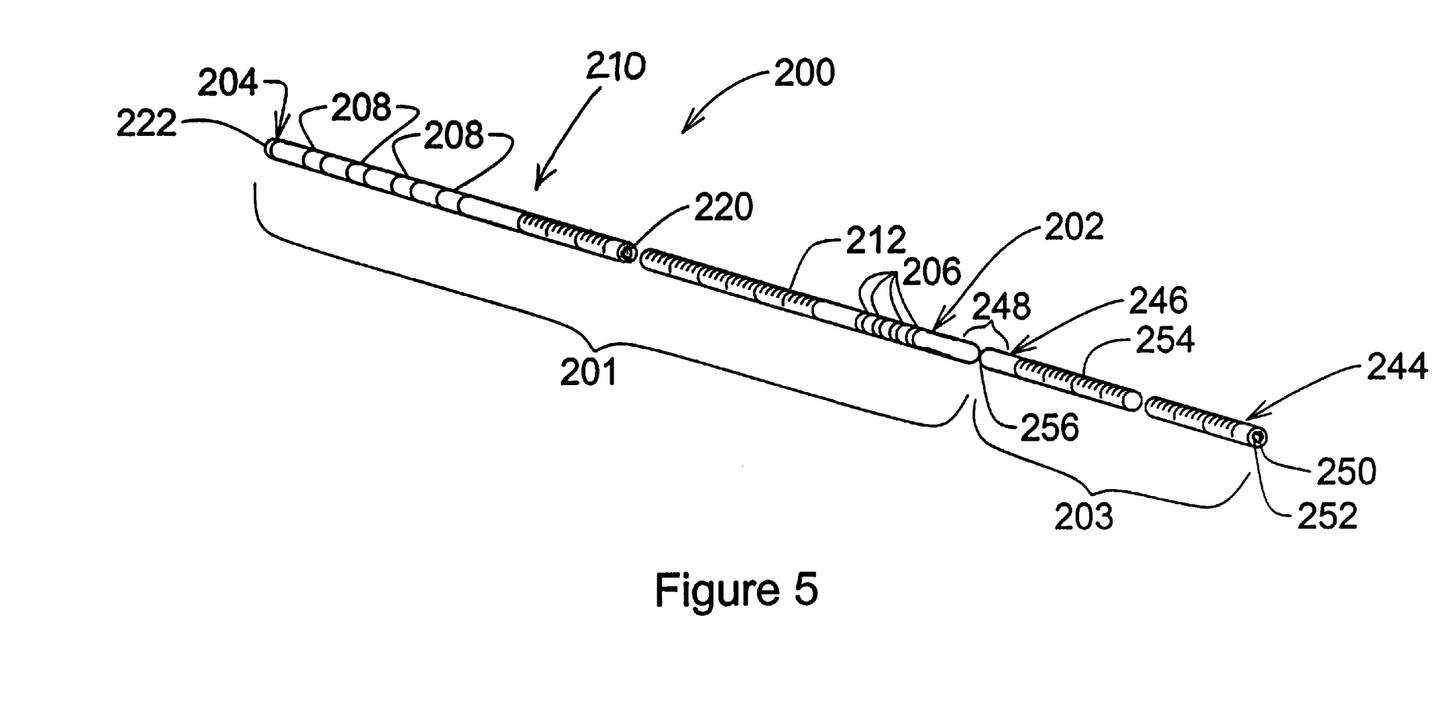
FIG. 5 is a lead of the present invention.

Referring now to FIG. 5, an implantable medical lead 200 according to another embodiment is illustrated. The lead 200 includes a lead portion 201 and an extension 203 removably coupled to the lead portion 201. The lead portion 201 is similar to the lead 100 described with respect to FIGS. 2–4 and like numerals are used to refer to like elements. The lead portion 201 includes a proximal end 202, a distal end 204, and a body 201 therebetween. The proximal end 202 includes a plurality of electrically conductive terminals 206 for operatively coupling the proximal end 202 to a neuro-stimulator device that is implanted in the patient's cranium or some kind of equipment. The distal end 204 includes at least one electrically conductive electrode 208 to electrically stimulate or for sensing the patient's brain. Typically, each terminal 206 is electrically connected to a single electrode 208 by a conductor (not shown), however, a terminal 206 can be connected to two or more electrodes 208. The conductor exhibits the desired mechanical properties of low resistance, corrosion, resistance, flexibility, and strength. Terminals 206, electrodes 208 and conductors are preferably formed of a non-corrosive, highly conductive material such as stainless steel, platinum, or platinum alloys such as a platinum-iridium alloy. It should further be noted that sensors other than electrodes 208 may be employed on some or all of the distal end 204. For example, a temperature sensor (e.g., a thermocouple), a chemical concentration sensor (such as a dissolved oxygen sensor), or a pressure sensor may be advantageously employed in lieu of one or more of the distal electrodes 208 in some variations.

The body 201 is made primarily from a medical grade, substantially inert material such as silicone, urethane or any of a number of suitable biocompatible materials. The body 201 provides a flexible and durable exterior structure for the components of the lead 200 and insulate adjacent terminals 206 and/or electrodes. Serving as a sheath, the body 201 contains the internalized elements of the lead portion 201. For example, the body 201 provides an enclosure for each conductor that connects a terminal 206 with one or more electrodes 208.

The body 201 of the lead portion 201 has a diameter between approximately 0.5 mm and approximately 2.0 mm, preferably has a diameter between 1.0 and 1.3 mm. In general, a smaller diameter is better, consistent with sufficient ruggedness and ease of handling for surgical applications. A suitable overall length for the lead portion 201 is between approximately 250 and 500 mm. In one variation, the body 201 further includes a plurality of markings 212 of the type described with respect to FIGS. 2–5 above. The markings 212 are preferably graduated markings 212 located along the outside of the body 201, preferably between the electrodes 208 and terminals 206. The longitudinal cross section of the lead 201 representative of the distal end 204 and proximal end 206 is similar to the cross-section depicted in FIG. 3.

A portion of the distal end 204 includes a reinforcing tube (not shown) preferably fabricated from a more rigid polymer material such as polyamide, polyimide, or polyetheretherketone (PEEK). Together the body 201 and the tube define a longitudinal lumen 220, which may be employed to receive a stylet to facilitate implantation. A stylet may not always be necessary, especially if the distal end 204 is sufficiently rigid from the use of a helical conductor set (not shown) and/or reinforcing tube.

The tip of the distal end 204 is closed by a relatively rigid plug 222 adapted to fit within the reinforcing tube, or if no such tube is present, the plug 222 is adapted to fit within the body 201. The plug 222 is preferably fabricated from a relatively rigid biocompatible polymer, and is crimped, glued, molded, or fused in place. It should be observed that numerous materials are possible for the plug 222, body 201, and reinforcing tube. Various categories of polymers and plastics such as polyester, polyimide, polyamide, polyetheretherketone (PEEK), and specific materials falling into those categories such as nylon are particularly well suited.

The lead portion 201 is removably coupled to an extension 203. The removable extension 203 includes a proximal end 244 and a distal end 246. The distal end 246 of the extension 203 is removably coupled to the proximal end 202 of the lead portion 201 at a separation zone or break-away zone 248. The extension 203 includes a lumen 250 extending longitudinally along the length of the extension 203 from the proximal end 244 of the extension 203 to the distal end 246 of the extension 203. The proximal end 244 of the extension 203 includes a lumen opening 252 for receiving a stylet. At the distal end 246 of the removable extension 203, the lumen 250 of the extension 203 connects with the lumen 220 of the lead portion 201 allowing a stylet to pass through the extension 203 and into the lead portion 201.

The removable extension 203 has a diameter that is substantially the same as the diameter of the lead portion 201. The diameter of the removable extension 203 is between approximately 0.5 mm and approximately 2.0 mm, preferably has a diameter between 1.0 and 1.3 mm. In one variation, the break-away zone 248 has a reduced diameter as discussed below. A suitable overall length for the removable extension 203 is at least as long as the length of a standard cannula or approximately 250 and 500 mm. In one variation, the removable extension 203 further includes a plurality of markings 254 of the type described with respect to FIGS. 2–5 above. The markings 254 are preferably graduated 254 markings located along the outside of the extension 203. In one variation, the lead portion 201 includes markings 212 and the extension 203 does not. In another variation, the extension 203 includes markings 254 and the lead portion 201 does not. In yet another variation, the lead portion 201 includes markings 212 and the extension 203 includes markings 254. Markings 212 on the lead portion 201 can be used independently from the markings 254 on the extension 203 and markings 254 on the extension 203 can be used independently of markings 212 on the lead portion 201. Also, the markings 212 on the lead portion 201 can be used in combination with the markings 254 on the extension 203. It should be noted that the markings on the lead portion can be used with or without an extension and vice versa.

The extension 203 is made from medical grade, substantially inert material such as silicone, urethane or any of a number of suitable biocompatible materials and provides a flexible and durable structure. The extension 203 is made from the same material having the same characteristics as the body 201 of the lead portion 201. Alternatively, the same material as the lead portion 201 or material different from the lead portion 201 having different characteristics is employed. In essence, the material of the removable extension 203 is customized to provide the desired flexibility, durability and ease of installation. In one variation, for example, the removable extension 203 is less flexible than the lead portion 201. A stiffer removable extension 203 relative to the lead portion 201 helps guide the lead portion 201 into position.

The removable extension 203 is removably coupled to the lead portion 201 in a connecting yet separable fashion to the proximal end 202 of the lead portion 201. This can be accomplished in a variety of ways. For example, the removable extension 203 may be coupled to the lead portion 201 with adhesive. Alternatively, the removable extension 203 is coupled to the lead portion 201 in a snap-fit engagement. In another example, the removable extension 203 is coupled to the lead portion 201 in a compression-fit engagement. In yet another example, the removable extension 203 is crimped to the lead portion 201. Also, the removable extension 203 can be coupled to the lead portion 201 in a friction-fit engagement. Any suitable connecting yet separable fashion is within the scope of the invention for connecting the removable extension 203 to the lead portion 201. The removable extension 203 is removed by application of manual force or with a removal tool such as scissors. The amount of force required to remove the extension 203 is generally greater than the force endured by the lead 200 during normal implantation such that the extension 203 will not be accidentally separated from the lead portion 201. The removable extension 203 is either integrally formed with the lead portion 201 or formed separately from the lead portion 201 and then removably coupled to the lead portion 201.

As shown in FIG. 5, the body 201 of the lead portion 201 is integrally formed with the removable extension 203 wherein the break-away zone 248 includes a score 256 for facilitating removal of the extension 203. As a result of the score 256, the break-away zone 248 has a reduced diameter or cross-sectional area of material at the break-away zone 248 that effectively weakens the break-away zone 248. The score 256 also provides a visual indicator of break-away zone 248. Alternatively, the break-away zone 248 is not substantially weaker relative to the remainder of the extension 203 and/or the lead portion 201. In such a variation, the extension 203 is preferably removed from the lead portion 201 with a removal tool and the score 256 or other marking serves as a visual indicator for an ideal separation point. Methods other than scoring are also possible. For example, forming a groove by molding or machining, cutting a notch or forming a crimp are within the scope of the invention for creating a visual indicator and/or a break-away zone 248 that is weaker or visually defined relative to the lead portion 201 and/or remaining portion of the extension 203.

Figure 6:
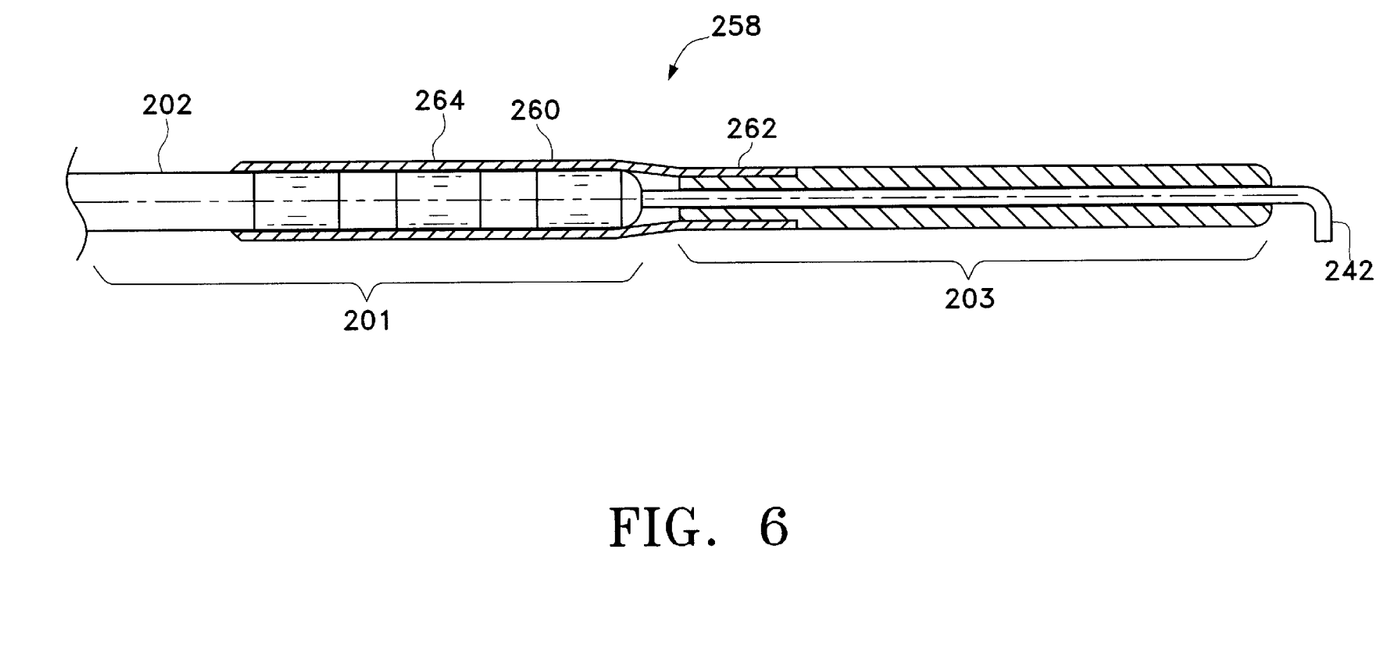
FIG. 6 is a cross-sectional view of a lead of the present invention.

Referring now to FIG. 6, there is shown another variation of a separation zone or break-away zone 258 in which the removable extension 203 is removably coupled to the lead portion 201. In this variation the removable extension 203 includes a sleeve portion 260 having a fixed end 262 and a lead portion receiving end 264. The fixed end 262 of the sleeve 260 is fixed to the distal end 246 of the extension 203. The lead portion receiving end 264 receives the lead portion 201 such that the lead portion 201 is retained in the lead portion receiving end 264. The lead portion 201 is removably retained in the lead portion receiving end 264 such that the extension 203 is coupled to the lead portion 201 in a compression-fit engagement. Alternatively, the removable extension 203 can be coupled in a separable fashion to the lead portion 201 in a variety of ways. For example, the removable extension 203 may be coupled to the lead portion 201 with adhesive. Alternatively, the removable extension 203 is coupled to the lead portion 201 in a snap-fit engagement. In yet another example, the removable extension 203 is crimped to the lead portion 201. Also, the removable extension 203 can be coupled to the lead portion 201 in a friction-fit engagement. Any suitable connecting yet separable fashion is within the scope of the invention for removably coupling the removable extension 203 to the lead portion 201. In one variation, the break-away zone includes a split-sleeve. The split sleeve, for example, can be employed in a compression-fit engagement or adhered using adhesive.

The removable extension 203 is removed by application of manual force such as with a pulling force or with a removal tool. The amount of force required to remove the extension 203 is generally greater than the force endured by the lead 200 during normal implantation such that the extension 203 will not be accidentally separated from the lead portion 201.

Figure 7A:
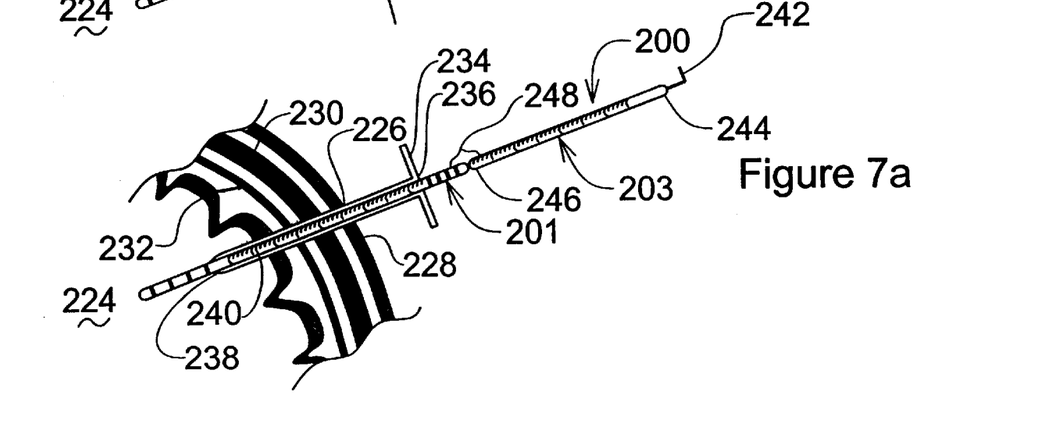
FIGS. 7a–7d illustrate a lead placement technique of the present invention.

The general procedure for implanting the lead in the brain is now discussed in reference to FIGS. 7a–7d. An electrode site 224 within the brain tissue is chosen. The site is chosen at any appropriate stage of the surgical procedure, including pre-surgically in an operative planning stage; intraoperatively after a craniotomy has been performed or a burr hole 226 has been made; or intraoperatively after one or more other procedures, such as functional mapping, have been performed. Referring first to FIG. 7a, after an incision in the patient's scalp 228 is formed, an insertion site or bore hole 226 is formed in a patient's cranium 230. An incision is made in the dura mater 232 and a cannula 234 is inserted.

The cannula 234 may be of any commercially available type. Generally, it has an open proximal end 236, an open distal end 238, and a central bore 240. Prior to insertion, the cannula 234 may be provided with an obturator (not shown) to assist in penetrating the tissue structure. The obturator is inserted into the central bore 240 of the cannula 234 to close the central bore 240 of the cannula 234 and prevent tissue from entering the cannula 234 during insertion.

Still referencing FIG. 7a, with the cannula 234 in position and the obturator removed, a brain lead 200 is passed into the bore 240 of the cannula 234 until positioned in a desired deep brain structure. The positioning of the brain lead 200 is assisted with a stylet 242. The stylet 242, or guide wire is inserted into the lumen 250 of the extension 203 and into the lumen 220 of the lead portion 201 to assist in positioning the lead portion 201. The lead 200 is gently pushed and guided into the cannula to the electrode site 224 with the stylet 242. The positioned brain lead 200 is shown in FIG. 7a. Alternate methods and devices may be used to achieve similar results.

As seen in FIG. 7a, the markings 212, 254 on the body 201 of the lead portion 201 and/or on the extension 203 provide the physician with a visual indicator of how much of the brain lead 200 has been inserted. The markings 212, 254 appearing outside of the cannula 234 are viewed. Also, in one variation, markings 212, 254 that are not outside of the cannula 234 are viewed using X-ray, fluoroscopy, and other known techniques during the installation. If the extension 203 includes markings 254 and the lead portion 201 does not, then the markings 254 are used. Also, if the lead portion 201 includes markings 212 and the extension does not, then the markings 212 are used by the physician. If both the lead portion 201 and the extension 203 include markings 212 and 254, respectively, then either the markings 212 or the markings 254 may be employed by the physician in positioning the lead. By viewing the markings 212, 254 at any location along the lead portion 201 and/or extension 203 at any stage of the implantation procedure facilitates accurate placement and positioning of the lead 200. Also, with the brain lead 200 in position, the markings 212, 254 serve as indicator in the event the brain lead 200 is accidentally moved during the remainder of the procedure and after the procedure is completed.

Figures 7B, 7C:
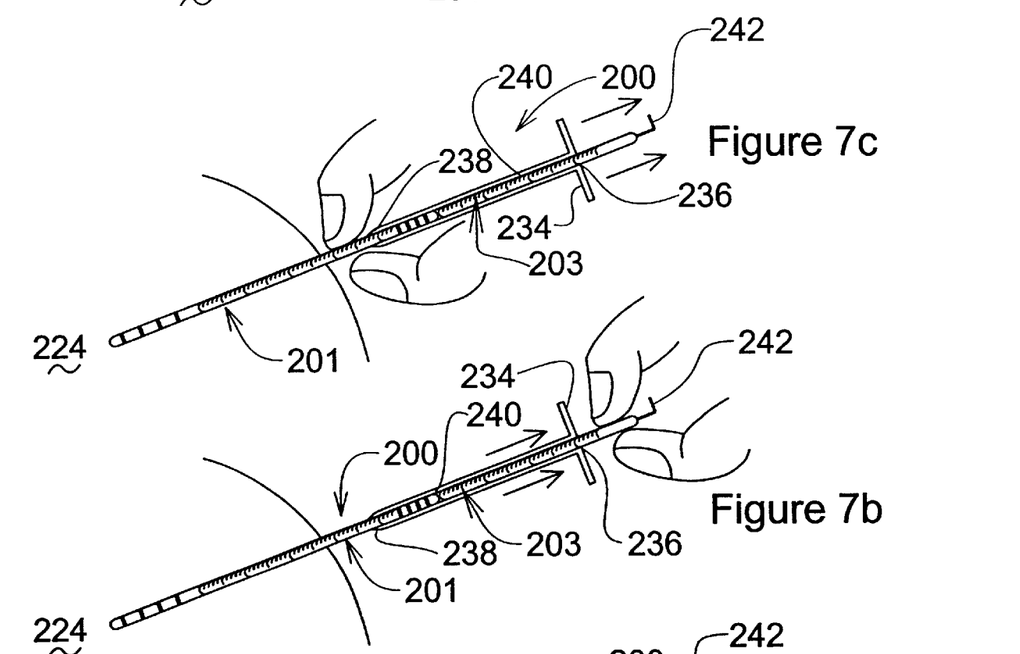

Referring now to FIG. 7b, after the cannula 234 and lead portion 201 is appropriately placed, the cannula 234 is retracted. As the cannula 234 is retracted, a stylet 242 is employed to hold the lead 200 in place at a proximal end 244 of the extension 203. The lead 200 and its position within the brain must be continually monitored to ensure proper placement.

After the cannula 234 is retracted such that its distal end 238 of the cannula 234 is exposed at the insertion site as shown in FIGS. 7b and 7c, the physician releases the stylet 242 and grasps the exposed portion of the lead portion 201 adjacent to the distal end 238 of the cannula 234. The physician holds the lead portion 201 in position so that the cannula 234 can be removed by sliding it longitudinally over the lead portion 201 and the extension 203. The markings 212, 254 on the brain lead 200 assist in keeping the brain lead 200 stationary by providing a visual indication of whether the brain lead 200 has been moved while the cannula 234 is being extracted.

Figure 7D:
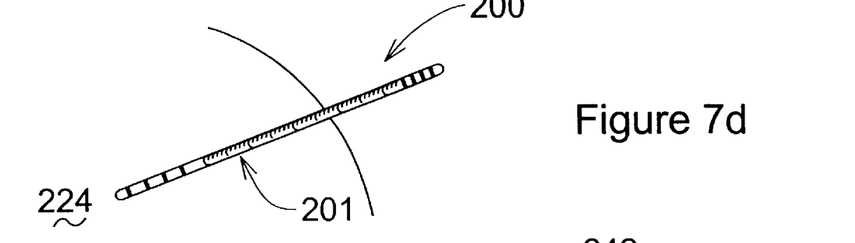

Next, the stylet 242 must be removed without grossly affecting the positioning of the lead 200. A positioned lead 200 with the stylet 242 removed is shown in FIG. 7d. Again, the markings 212, 254 on the lead portion 201 and/or extension 203 assist in maintaining the lead portion 201 in position as the stylet 242 is removed from the lumen 220 of the lead portion 201 and the lumen 250 of the extension 203. Also, fine positioning of lead portion 201 either before or after removal of the stylet 242 is aided by the markings 212, 254 as they are viewed outside the brain or within the brain with the aid of viewing instrumentation.

Finally, the extension 203 is removed by applying a force sufficiently large to separate the extension 203 from the lead portion 201 at the break-away zone 248. Alternatively, a removal tool is employed to sever the extension 203 at the break-away zone 248. With the extension 203 removed, the terminals 206 at the proximal end 202 of the lead portion 201 are ready to be connected to an implantable neurostimulator device that is or is not implanted in the patient's cranium or to other equipment.

The extension 203 serves as a sacrificial segment that is discarded after the implantation of the lead portion 201 is accomplished. Traditionally, the lead portion 201 is longer than minimally needed by approximately the length of the cannula 234 so that the cannula 234 can be removed while the lead portion 201 is held in position. With the extension 203 of the present invention, however, a shorter lead portion 201 is possible. Therefore, the extension 203 advantageously avoids a lead portion 201 that is too long for aesthetic reasons as well as for functional attachment to a cranially implanted neurostimulator device while increasing the ease of installation. Furthermore, post-installation, a shorter lead portion 201 reduces possible traction on the lead portion 201 that would potentially result if a longer lead portion 201 was connected to a neurostimulator device implanted in the same location of the cranium. Also, susceptibility to reliability problems may be reduced in the instant invention as compared to lead portions with an excess of coiled-up length. Furthermore, the extension 203 increases the ease of cannula 234 removal as well as lead portion 201 positioning.

While the present invention has been described with reference to one or more particular variations, those skilled in the art will recognize that many changes may be made thereto without departing from the spirit and scope of the present invention. Each of these embodiments and obvious variations thereof are contemplated as falling within the spirit and scope of the claimed invention, which is set forth in the following claims.

What is claimed is:

1. An implantable lead comprising:
   a body having a proximal end and a distal end;
   at least one electrode at the distal end;
   at least one terminal at the proximal end, the at least one electrode being connected to the at least one terminal; and
   a plurality of markings on the body, wherein the markings are proximal of the electrodes.

2. The implantable lead of claim 1 wherein the markings are graduated.

3. The implantable lead of claim 1 wherein the markings are located between the at least one electrode and the at least one terminal.

4. The implantable lead of claim 1 wherein the markings are printed using ion beam assisted deposition.

5. The implantable lead of claim 1 wherein the markings are formed using a silicone-based adhesive with carbon black pigment.

6. The implantable lead of claim 1 wherein the markings are radio-opaque.

7. An implantable lead comprising:
   a body having a proximal end and a distal end;
   at least one electrode at the distal end;
   at least one terminal at the proximal end, the at least one electrode being connected to the at least one terminal; and a plurality of markings providing an indication of lead position, wherein the markings are proximal of the electrodes.

8. A method of implanting a lead comprising the steps of:
   providing a lead having a proximal end and a distal end, the lead having at least one electrode at the distal end connected to at least one terminal at the proximal end, the lead further includes a plurality of markings located between the distal end and the proximal end;
   determining an electrode site for stimulation;
   providing an insertion site in a patient's cranium;
   inserting the lead into the insertion site;
   positioning the lead at the electrode site; and
   providing a visual indication of lead position by the markings on the lead.

9. An implantable lead comprising:
   a lead portion having a proximal end and a distal end, the lead portion further including a lead body between the proximal end and the distal end, at least one electrode at the distal end and at least one terminal at the proximal end, the at least one electrode being connected to the at least one terminal, and a plurality of markings on the lead body; and
   an extension removably connected to the lead portion, the extension having a proximal end, distal end, and an extension body between the proximal end and the distal end.

10. The implantable lead of claim 9 wherein the markings are radio-opaque.

11. The implantable lead of claim 9 wherein extension includes a plurality of markings on the body of the extension.

12. The implantable lead of claim 11 wherein the markings are radio-opaque.

13. The implantable lead of claim 9 wherein the extension is removably coupled to the lead portion such that the distal end of the extension is removably coupled to the proximal end of the lead portion.

14. The implantable lead of claim 9 wherein the lead portion includes a lumen and the extension includes a lumen, the lumen of the lead portion is interconnected with the lumen of the extension.

15. The implantable lead of claim 9 wherein the extension is more rigid than the lead portion.

16. The implantable lead of claim 9 wherein the at least one terminal of the lead portion is operatively connected to a neurostimulator device that is implanted in a patient's cranium.

17. An implantable lead comprising:
   a lead portion having a proximal end and a distal end, the lead portion further includes at least one electrode at the distal end electrically connected to at least one terminal at the proximal end; and
   an extension removably connected to the lead portion at a break-away zone, the extension having proximal end, a distal end, and a lumen extending therethrough, the lumen of the lead portion being interconnected with the lumen of the extension.

18. The implantable lead of claim 17 wherein the lead portion includes a lumen extending between the proximal end and the distal end of the lead portion.

19. The implantable lead of claim 17 wherein the break-away zone includes a score.

20. The implantable lead of claim 17 wherein the break-away zone includes a weakened area.

21. The implantable lead of claim 17 wherein the break-away zone includes a reduced cross-sectional area of material such that the break-away zone is weakened relative to other portions of the lead portion or extension.

22. The implantable lead of claim 17 wherein the break-away zone includes a visual indicator.

23. The implantable lead of claim 17 wherein the extension has a length between approximately 250 mm and approximately 500 mm.

24. An implantable lead comprising:
   a lead portion having proximal end and a distal end, at least one electrode at the distal end and at least one terminal at the proximal end, the at least one electrode being electrically connected to the at least one terminal; and
   an extension removably coupled to the lead portion, the extension having a proximal end and a distal end, the extension further including a sleeve portion having a fixed end and a lead portion receiving end, the fixed end being fixed to the distal end of the extension, the lead portion is removably coupled within the lead portion receiving end of the sleeve.

25. The implantable lead of claim 24 wherein the sleeve is split.

26. The implantable lead of claim 24 wherein the extension includes a lumen extending between the proximal end and distal end of the extension.

27. The implantable lead of claim 26 wherein the lead portion includes a lumen extending between the proximal end and distal end of the lead portion, the lumen of the lead portion being interconnected with the lumen of the extension.

28. A method of implanting a lead in a patient's brain comprising the steps of:
   providing a lead having a lead portion and an extension, the lead portion being removably coupled to the extension, the lead portion having at least one electrode at a distal end electrically coupled to at least one terminal at a proximal end;
   determining an electrode site for stimulation;
   providing an insertion site in a patient's cranium;
   inserting a cannula into the patient's brain;
   inserting the lead into the cannula such that the distal end of the lead portion is inserted first;
   positioning the lead at the electrode site;
   removing the cannula; and
   removing the extension from the lead portion.

29. The method of claim 28 wherein the extension includes a proximal end and a distal end, the extension further including a lumen extending between the proximal end and the distal end, the lead portion further including a lumen extending between the distal end and the proximal end of the lead portion, the lumen of the lead portion being interconnected with the lumen of the extension; and
   further including the step of inserting a stylet into the lumen of the extension and the lumen of the lead portion.

30. The method of claim 29 further including the step of removing the stylet.

31. The method of claim 28 wherein the lead includes markings, the step of positioning the lead at the electrode site includes observing the markings.

32. The method of claim 28 wherein the step of removing the extension from the lead portion includes using a removal tool.

33. The method of claim 28 further including the step of operatively connecting the at least one terminal to a neurostimulator device that is implanted in the patient's cranium.

34. An implantable lead comprising:
   a lead portion having a proximal end and a distal end, the lead portion further including a lead body between the proximal end and the distal end, at least one electrode at the distal end and at least one terminal at the proximal end, the at least one electrode being connected to the at least one terminal; and
   an extension removably connected to the lead portion, the extension having a proximal end, distal end, and a body between the proximal end and the distal end, and wherein the extension and the lead portion have substantially the same diameter.

* * * * *